United States Patent
Toyama et al.

(10) Patent No.: US 11,378,580 B2
(45) Date of Patent: Jul. 5, 2022

(54) PROTEIN DETECTION METHOD USING MASS SPECTROMETRY

(71) Applicant: SHIMADZU CORPORATION, Kyoto (JP)

(72) Inventors: Atsuhiko Toyama, Kyoto (JP); Taka-Aki Sato, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 0 days.

(21) Appl. No.: 15/119,616

(22) PCT Filed: Feb. 18, 2014

(86) PCT No.: PCT/JP2014/053780
§ 371 (c)(1),
(2) Date: Aug. 17, 2016

(87) PCT Pub. No.: WO2015/125216
PCT Pub. Date: Aug. 27, 2015

(65) Prior Publication Data
US 2017/0059579 A1    Mar. 2, 2017

(51) Int. Cl.
*G01N 33/68* (2006.01)
*C12Q 1/34* (2006.01)
*C12P 21/06* (2006.01)
*H01J 49/00* (2006.01)

(52) U.S. Cl.
CPC .......... *G01N 33/6848* (2013.01); *C12P 21/06* (2013.01); *C12Q 1/34* (2013.01); *G01N 33/6851* (2013.01); *C12Y 304/21014* (2013.01); *H01J 49/00* (2013.01)

(58) Field of Classification Search
CPC .. G01N 33/6848; G01N 33/6851; C12Q 1/34; C12P 21/06; C12Y 304/21014; H01J 49/00
See application file for complete search history.

(56) References Cited

U.S. PATENT DOCUMENTS

| 2008/0260894 | A1* | 10/2008 | Lim | A23K 1/1656 426/2 |
|---|---|---|---|---|
| 2009/0148951 | A1* | 6/2009 | Zhang | G01N 33/6848 436/86 |
| 2010/0015652 | A1 | 1/2010 | Granda et al. | |
| 2010/0047812 | A1 | 2/2010 | Van Eyk et al. | |
| 2010/0086938 | A1 | 4/2010 | Shimada et al. | |
| 2012/0009614 | A1 | 1/2012 | Zhang et al. | |
| 2012/0276570 | A1 | 11/2012 | Van Eyk et al. | |
| 2013/0203099 | A1 | 8/2013 | Zhang et al. | |

FOREIGN PATENT DOCUMENTS

| JP | 2010-515020 A | 5/2010 |
|---|---|---|
| JP | 4983803 B2 | 7/2012 |
| WO | 96/36732 A1 | 11/1996 |
| WO | WO 2007/124750 | 11/2007 |
| WO | WO 2008/005455 A2 | 1/2008 |
| WO | WO 2008/005455 A3 | 1/2008 |
| WO | 2008/079914 A1 | 7/2008 |
| WO | WO 2009/006568 | 1/2009 |

OTHER PUBLICATIONS

Macroglobulin. Alpha-2-Macroglobulin. Sino Biological Inc. 2012;1-3.*
Creighton TE. Stability of alpha-helices. Nature vol. 1987;326(9):547-548.*
Verdine et al. Stapled peptides for intracellular drug targets. Methods in Enzymology. 2012;503:3-33.*
WHO. Use of anticoagulants in diagnostic laboratory investigations. WHO/DIL/LAB/99.1 Rev.2. 2002;1-62.*
Shi et al. IgY14 and SuperMix immunoaffinity separations coupled with liquid chromatography-mass spectrometry for human plasma proteomics biomarker discovery. Methods. 2012;56(2):246-253.*
Sterling et al. Effects of Buffer Loading for Electrospray Ionization Mass Spectrometry of a Noncovalent Protein Complex that Requires High Concentrations of Essential Salts. J Am Soc Mass Spectrom. 2010;21(6):1045-1049.*
Extended European Search Report dated Aug. 8, 2017 in Patent Application No. 14882930.2.
Scott A. Gerberg, et al., "Absolute quantification of proteins and phosphoproteins from cell lysates by tandem MS," Proc. Natl. Acad. Sci. USA, vol. 100, No. 12, Jun. 10, 2003, pp. 6940-6945.
Tujin Shi, et al., "Antibody-free, targeted mass-spectrometric approach for quantification of proteins at low pictogram per milliliter levels in human plasma/serum," Proc. Natl. Acad. Sci. USA, vol. 109, No. 38, Sep. 18, 2012, pp. 15395-15400.
N. Leigh Anderson, et al., "Precision of Heavy-Light Peptide Ratios Measured by MALDI-TOF Mass Spectrometry," Journal of Proteome Research, vol. 11, Jan. 18, 2012, pp. 1868-1878.
Radhakrishna S. Tirumalai, et al., "Characterization of the Low Molecular Weight Human Serum Proteome," Molecular & Cellular Proteomics, vol. 2, No. 10, Aug. 13, 2003, pp. 1096-1103.
International Search Report dated May 27, 2014 in PCT/JP2014/053780 filed Feb. 18, 2014.
Office Action dated Mar. 29, 2019 in corresponding European Patent Application No. 14882930.2, filed Feb. 18, 2014, 5 pages.

* cited by examiner

*Primary Examiner* — Lynn Y Fan
(74) *Attorney, Agent, or Firm* — Morgan, Lewis & Bockius LLP

(57) ABSTRACT

The present invention provides: a method of pretreating a serum or plasma sample for detection of a protein or a plurality of proteins of interest in a serum or plasma sample via mass spectrometry and a method of detecting such a protein or proteins, wherein proteins such as albumin present in abundance in a sample are removed in a convenient manner, thereby making it possible to collect digested peptides from the protein of interest. Specifically, the present invention provides a method of pretreating a sample for detecting proteins in a serum or plasma sample via mass spectrometry, comprising a step of adding a protease to the sample under non-denaturing conditions to digest proteins and a step of separating the obtained peptides from undigested proteins, and a method of detecting proteins, comprising subjecting the obtained peptides to mass spectrometry.

19 Claims, 9 Drawing Sheets

Specification includes a Sequence Listing.

A

B

SEQUENCE LISTING

<160> NUMBER OF SEQ ID NOS: 12

<210> SEQ ID NO 1
<211> LENGTH: 319
<212> TYPE: PRT
<213> ORGANISM: Homo sapiens

<400> SEQUENCE: 1

Met Ala Thr Lys Gly Gly Thr Val Lys Ala Ala Ser Gly Phe Asn Ala
1               5                   10                  15

Met Glu Asp Ala Gln Thr Leu Arg Lys Ala Met Lys Gly Leu Gly Thr
            20                  25                  30

Asp Glu Asp Ala Ile Ile Ser Val Leu Ala Tyr Arg Asn Thr Ala Gln
        35                  40                  45

Arg Gln Glu Ile Arg Thr Ala Tyr Lys Ser Thr Ile Gly Arg Asp Leu
    50                  55                  60

Ile Asp Asp Leu Lys Ser Glu Leu Ser Gly Asn Phe Glu Gln Val Ile
65                  70                  75                  80

Val Gly Met Met Thr Pro Thr Val Leu Tyr Asp Val Gln Glu Leu Arg
            85                  90                  95

Arg Ala Met Lys Gly Ala Gly Thr Asp Glu Gly Cys Leu Ile Glu Ile
            100                 105                 110

Leu Ala Ser Arg Thr Pro Glu Glu Ile Arg Arg Ile Ser Gln Thr Tyr
        115                 120                 125

Gln Gln Gln Tyr Gly Arg Ser Leu Glu Asp Asp Ile Arg Ser Asp Thr
            130                 135                 140

Ser Phe Met Phe Gln Arg Val Leu Val Ser Leu Ser Ala Gly Gly Arg
145                 150                 155                 160

Asp Glu Gly Asn Tyr Leu Asp Asp Ala Leu Val Arg Gln Asp Ala Gln
                165                 170                 175

Asp Leu Tyr Glu Ala Gly Glu Lys Lys Trp Gly Thr Asp Glu Val Lys
            180                 185                 190

Phe Leu Thr Val Leu Cys Ser Arg Asn Arg Asn His Leu Leu His Val
                195                 200                 205

Phe Asp Glu Tyr Lys Arg Ile Ser Gln Lys Asp Ile Glu Gln Ser Ile
            210                 215                 220

Lys Ser Glu Thr Ser Gly Ser Phe Glu Asp Ala Leu Leu Ala Ile Val
225                 230                 235                 240

Lys Cys Met Arg Asn Lys Ser Ala Tyr Phe Ala Glu Lys Leu Tyr Lys
                245                 250                 255

Ser Met Lys Gly Leu Gly Thr Asp Asp Asn Thr Leu Ile Arg Val Met
            260                 265                 270

Val Ser Arg Ala Glu Ile Asp Met Leu Asp Ile Arg Ala His Phe Lys
275                 280                 285

Arg Leu Tyr Gly Lys Ser Leu Tyr Ser Phe Ile Lys Gly Asp Thr Ser
            290                 295                 300

Gly Asp Tyr Arg Lys Val Leu Leu Val Leu Cys Gly Gly Asp Asp
305                 310                 315

<210> SEQ ID NO 2
<211> LENGTH: 15
<212> TYPE: PRT
<213> ORGANISM: Homo sapiens

<400> SEQUENCE: 2

Ala Ala Ser Gly Phe Asn Ala Met Glu Asp Ala Gln Thr Leu Arg
1               5                   10                  15

<210> SEQ ID NO 3
<211> LENGTH: 16
<212> TYPE: PRT
<213> ORGANISM: Homo sapiens

<400> SEQUENCE: 3

Gly Leu Gly Thr Asp Glu Asp Ala Ile Ile Ser Val Leu Ala Tyr Arg
1               5                   10                  15

<210> SEQ ID NO 4
<211> LENGTH: 11
<212> TYPE: PRT
<213> ORGANISM: Homo sapiens

<400> SEQUENCE: 4

Ile Ser Gln Thr Tyr Gln Gln Gln Tyr Gly Arg
1               5                   10

<210> SEQ ID NO 5
<211> LENGTH: 9
<212> TYPE: PRT
<213> ORGANISM: Homo sapiens

<400> SEQUENCE: 5

Ser Asp Thr Ser Phe Met Phe Gln Arg
1               5

```
<210> SEQ ID NO 6
<211> LENGTH: 10
<212> TYPE: PRT
<213> ORGANISM: Homo sapiens

<400> SEQUENCE: 6

Val Leu Val Ser Leu Ser Ala Gly Gly Arg
1               5                   10

<210> SEQ ID NO 7
<211> LENGTH: 12
<212> TYPE: PRT
<213> ORGANISM: Homo sapiens

<400> SEQUENCE: 7

Asp Glu Gly Asn Tyr Leu Asp Asp Ala Leu Val Arg
1               5                   10

<210> SEQ ID NO 8
<211> LENGTH: 16
<212> TYPE: PRT
<213> ORGANISM: Homo sapiens

<400> SEQUENCE: 8

Ser Glu Thr Ser Gly Ser Phe Glu Asp Ala Leu Leu Ala Ile Val Lys
1               5                   10                  15

<210> SEQ ID NO 9
<211> LENGTH: 11
<212> TYPE: PRT
<213> ORGANISM: Homo sapiens

<400> SEQUENCE: 9

Gly Leu Gly Thr Asp Asp Asn Thr Leu Ile Arg
1               5                   10

<210> SEQ ID NO 10
<211> LENGTH: 9
<212> TYPE: PRT
<213> ORGANISM: Homo sapiens

<400> SEQUENCE: 10

Ala Glu Ile Asp Met Leu Asp Ile Arg
1               5

<210> SEQ ID NO 11
<211> LENGTH: 8
<212> TYPE: PRT
<213> ORGANISM: Homo sapiens

<400> SEQUENCE: 11

Gly Asp Thr Ser Gly Asp Tyr Arg
1               5

<210> SEQ ID NO 12
<211> LENGTH: 15
<212> TYPE: PRT
<213> ORGANISM: Artificial
<220> FEATURE:
<223> OTHER INFORMATION: internal standard
```

```
<400> SEQUENCE: 12

Pro Pro Pro Pro Pro Pro Pro Pro Pro Pro Pro Pro Pro Pro Arg
1               5                   10                  15
```

PROTEIN DETECTION METHOD USING MASS SPECTROMETRY

TECHNICAL FIELD

The present invention relates to a method of detecting proteins in a sample via mass spectrometry (MS). More specifically, the present invention relates to a method of detecting and identifying proteins via high-performance liquid chromatograph mass spectrometry (LC/MS) or matrix-assisted laser desorption/ionization (MALDI).

BACKGROUND ART

In recent years, along with the remarkable evolution of mass spectrometers, the assay of proteins that serve as biomarkers for diseases typified by cancers has been studied using systems of mass spectrometry that can replace conventional immunoassay (assay systems based on the antibody-antigen reaction). Mass spectrometry enables simultaneous quantitative determination of a plurality of biomarker proteins. Therefore, it has been expected to bring about effects of eliminating the time lag between the identification of potential biomarkers, and the construction of an immunoassay system, which is necessary for conventional methods, allowing acquisition of information on changes in the quality of proteins, and increasing determination accuracy through the assay of a plurality of biomarkers.

One method of detecting blood proteins using a mass spectrometer is a method in which impurities that inhibit ionization are removed from a serum sample, proteins are ionized by matrix-assisted laser desorption ionization or electrospray ionization (ESI), and quantitative analysis is performed using the signal intensity for each of the peaks resolved based on the mass/charge ratio of the protein ion. Such method allows automatic analysis of a plurality of specimens using a system in which a plate used for pretreatment is directly introduced into a mass spectrometer (SELDI Protein Chip® System: Patent Literature 1). However, the method is disadvantageous in that there are not many types of proteins that can be detected, and the detection of trace components is difficult.

In another method, a system in which a protein of interest is directly assayed after the protein is isolated and purified from a sample such as serum using an antibody that specifically binds to the protein has been suggested (Patent Literature 2). In this case, the use of the antibody allows detection of trace components. However, the production of antibodies which can withstand enrichment of trace components is the rate-limiting factor, and the problems of conventional immunoassay still remain unresolved.

Meanwhile, a method in which analysis is carried out after fragmentation of a protein with a protein-digesting enzyme (protease) into short peptide chains is a technique that has been established for protein identification and acquisition of protein conformation information. In particular, there is a method in which mass spectrometry (MS) is performed to determine the mass of a peptide group obtained by digesting a biological sample with a protease, the amino acid sequence is determined preferably by tandem MS analysis, and proteins present in the original sample are estimated by matching information against data in a database. This is referred to as shotgun proteomics, and has been widely used in biological research.

In recent years, a quantitative analysis method for estimating the amount of the original protein by quantitatively determining digested peptides has been established for shotgun proteomics (Non-Patent Literature 1). This method allows for high sensitivity because the analyte is a peptide that is easily ionized, and highly accurate quantification is realized by using an internal standard labeled with a stable isotope. Further, assay system sensitivity has been dramatically improved, such that sensitivity on the femtomole-or-smaller scale can be achieved by connecting a mass spectrometer to a device for nanoscale liquid chromatography for peptide separation and continuously carrying out assay in response to peptide elution.

In general, in order to efficiently achieve protein fragmentation via protease treatment, denaturation treatment with heat, pH conditions, or denaturing agents, reduction treatment for disulfide bond cleavage with dithiothreitol (DTT), 2-mercaptoethanol (2-ME), or Tris(2-carboxyethyl)phosphine hydrochloride (TCEP), alkylation treatment for thiol group protection and maintenance of an irreversibly dissociated state with the use of iodoacetamide (2-iodoacetamide: IAA), and the like are carried out prior to protease treatment.

In biological samples, a variety of proteins coexist at different concentrations. In particular, the blood protein concentration is within the $10^9$-order range. Meanwhile, the dynamic range that allows capture of proteins by a mass spectrometer is in a concentration range between the $10^3$-order and the $10^4$-order. Therefore, the detection of trace proteins in blood by mass spectrometry is extremely difficult.

For example, if the above method is applied to a serum sample to substantially completely fragmentate proteins in the sample, peptides from proteins contained at high concentrations such as albumin would account for the majority of the resulting product, causing saturation of the analysis system. In particular, albumin is known to account for over 50% of all blood proteins. Accordingly, when conventional pretreatment is performed to detect the peptides, most of peaks are those derived from albumin, which makes it very difficult to detect peaks from a protein of interest contained in a trace amount.

In order to solve the above problem, a method in which fine fractions of digested peptides are obtained by multi-stage purification to intensively analyze a small fraction enriched from all of the fractions (Non-Patent Literature 2) and a method in which enrichment is carried out at the peptide level involving immunoprecipitation using an antibody that specifically binds to a peptide of interest or ion exchange chromatography (Non-Patent Literature 3) have been proposed. However, these methods deviate from the scope of throughput and cost requirements for clinical examination because they involve very complicated pretreatment.

That is, also with regard to the aforementioned methods, the way in which easy reduction of the concentration range of proteins in serum samples is achieved constitutes a key factor for imparting versatility to the quantitative determination of proteins such as biomarkers by mass spectrometry. To date, there have been no reported technologies that allow the detection efficiency of a peptide of interest to be improved through convenient, high-speed treatment using serum or plasma as a sample and without the use of antibodies.

CITATION LIST

Patent Literature

Patent Literature 1: WO1996/036732
Patent Literature 2: JP Patent No. 4983803

Non-Patent Literature

Non-Patent Literature 1: Proc Natl Acad Sci USA 2003, 100 (12), 6940-5
Non-Patent Literature 2: Proc Natl Acad Sci USA 2012, 109 (38), 15395-400
Non-Patent Literature 3: J Proteome Res 2012, 11 (3), 1868-78

SUMMARY OF INVENTION

Technical Problem

An object of the present invention is to provide a method of pretreating a serum or plasma sample for detection of a protein or a plurality of proteins of interest in a serum or plasma sample via mass spectrometry and a method of detecting such a protein or proteins, wherein proteins such as albumin present in abundance in a sample are removed in a convenient manner, thereby making it possible to collect digested peptides from the protein of interest.

Solution to Problem

As a result of intensive studies for various assay methods to achieve the above object, the present inventors have surprisingly found that it is possible to securely obtain peptides necessary for quantitative determination of a protein of interest, by adding a protease directly to serum or plasma so as to prevent generation of peptides from albumin and the like under conditions that allow minimized dilution and denaturation of serum or plasma with the use of a buffering agent. Further, it is possible to relatively increase the proportion of peptides derived from the protein of interest by removing undigested proteins after protease treatment.

The method of the present invention provided remarkable results that albumin contained in abundance in serum and plasma is not digested, and therefore no albumin-derived peptide peaks are detected when mass spectrometry is conducted. Specifically, the method of the present invention is a method of simultaneously performing specific digestion and enrichment of proteins of interest based on sensitivity to protease digestion. This makes it possible to assay proteins with low blood concentrations in an assay system for detecting and quantitatively determining proteins of interest via mass spectrometry in a very convenient manner, compared with conventional methods.

Specifically, embodiments of the present invention are as follows.
1. A method of pretreating a sample for detecting proteins in a serum or plasma sample via mass spectrometry, comprising a step of adding a protease to the sample under non-denaturing conditions to digest proteins and a step of separating the obtained peptides from undigested proteins.
2. A method of detecting proteins in a serum or plasma sample via mass spectrometry, comprising: a step of adding a protease to the sample under non-denaturing conditions to digest proteins; a step of separating the obtained peptides from undigested proteins; and a step of subjecting the peptides to mass spectrometry.
3. The method according to 1 or 2 above, which does not comprise a protein or peptide enrichment step before and/or after protease treatment.
4. The method according to any one of 1 to 3 above, wherein the protease is trypsin.
5. The method according to any one of 1 to 4 above, wherein an immobilized enzyme is used as the protease.
6. The method according to any one of 1 to 5 above, wherein α2 macroglobulin is present in the sample.
7. The method according to any one of 1 to 6 above, wherein analysis is conducted via LC/MS or MALDI-TOF
8. The method according to any one of 1 to 7 above, wherein MS/MS analysis is conducted.
9. The method according to any one of 1 to 8 above, wherein albumin is not digested.

Advantageous Effects of Invention

In contrast to conventional methods that pursue efficient fragmentation of proteins, the present invention is based on the finding that remarkable results for protein detection using mass spectrometry can be obtained under conditions that are unlikely to cause digestion by protease.

According to the present invention, it has become possible to quantitatively determine trace proteins in a sample without carrying out a step of protein or peptide enrichment or requiring conventionally used pretreatment such as denaturation, reduction, or alkylation of proteins. This enables reduction of the time and cost required for pretreatment, thereby providing a high-throughput quantitative determination method.

DESCRIPTION OF EMBODIMENTS

Figure 1:
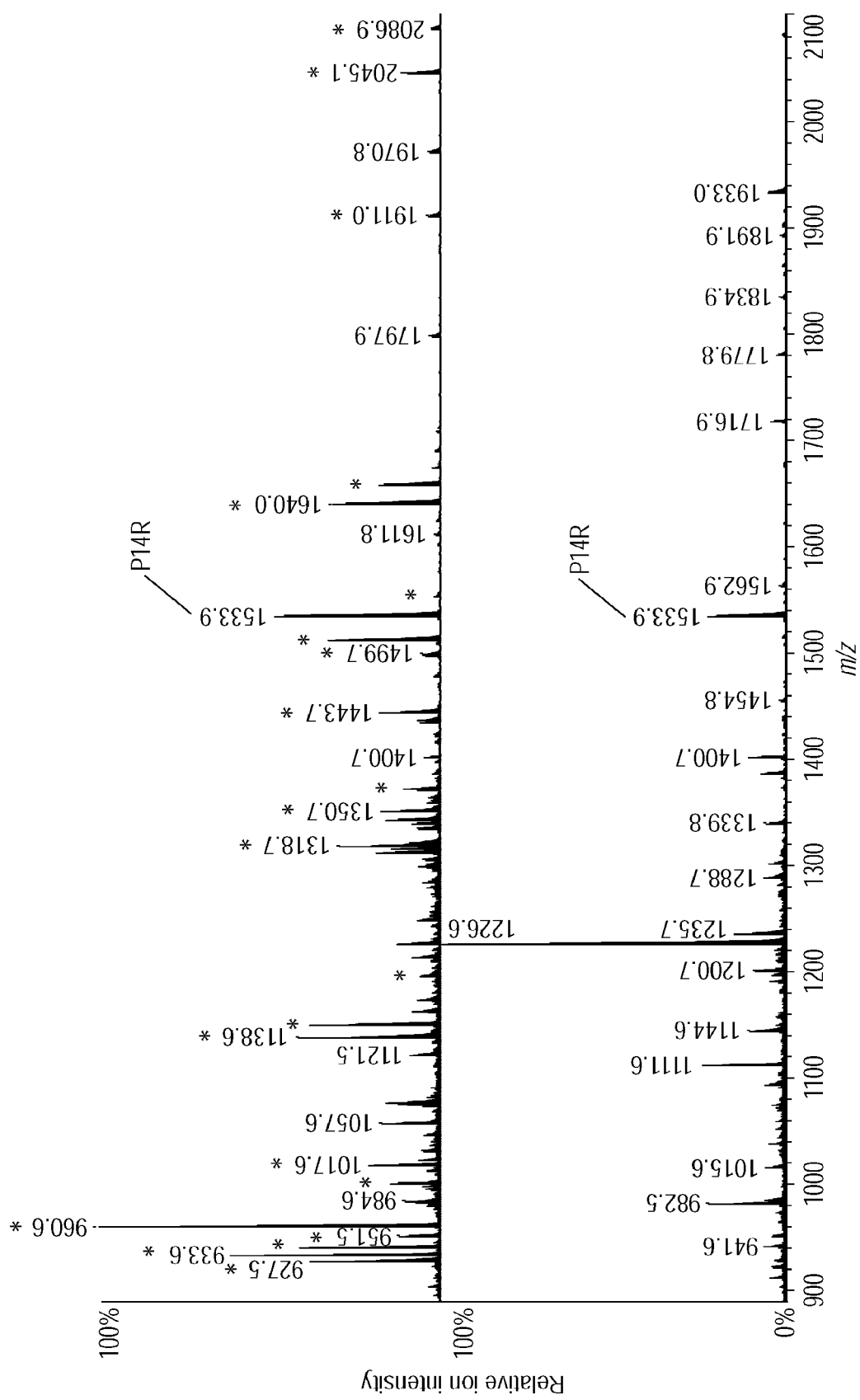
FIG. 1 shows the mass spectra of the digested serum peptides obtained by the pretreatment method of the present invention and the conventional pretreatment method. The asterisks (*) denote albumin-derived peaks among the observed peaks. Samples were spiked with P14R (SEQ ID NO: 12, m/z 1533.9) as an internal standard after desalting. The upper spectrum represents the results obtained by the conventional method and the lower spectrum represents the results obtained by the method of the present invention.

The terms used herein are used in the sense normally used in the art unless otherwise specified herein.

The expression "serum or plasma sample" used herein refers to a sample from blood collected from a subject for the purpose of detecting the presence of a protein of interest, which is serum or plasma per se or a serum- or plasma-derived sample. Those skilled in the art would understand that such samples also include, for example, a sample to which an agent has been added for preservation of the sample or the like. Examples of subjects include, but are not limited to, mammals and especially humans.

As described above, in the conventional method, a serum or plasma sample is subjected to protein denaturation, reduction, and alkylation treatments, and then protease treatment, prior to the detection of a protein of interest. In addition, in order to detect trace proteins or peptides, enrichment of proteins or peptides is appropriately carried out by immunoprecipitation, ion-exchange chromatography, or the like, before and/or after protease treatment. Further, an enzymatic digestion reaction buffer is generally added for digestion of proteins with proteases so that a reaction solution can be adjusted to serve as an environment with appropriate pH and ionic strength. For example, for reaction with trypsin, an ammonium bicarbonate solution, Tris buffer, and the like are often used for the purpose of pH adjustment. In the conventional method, it is further necessary to carry out additional treatment to prevent a reagent that has been added for pretreatment, and especially high-concentration urea or a surfactant that has been added for denaturation, from affecting protease treatment and mass spectrometry.

The term "denaturation" (of proteins) used herein refers to cases in which a protein conformation loses its higher-order structure originally observed in vivo and such structure undergoes alteration. For example, it is known that not only rapid changes in ion intensity, pH, and temperature but also the addition of high-concentration chaotropic agents and surfactants may cause denaturation.

The present invention provides a pretreatment method including a step of digesting a serum or plasma sample with the addition of a protease under non-denaturing conditions for proteins and a step of separating the resulting peptides from undigested proteins, and a method of detecting proteins via mass spectrometry including a step of subjecting the obtained peptides to mass spectrometry. Preferably, the methods of the present invention do not include a step of protein or peptide enrichment, which has been carried out before and/or after protease treatment in the conventional methods.

The term "non-denaturing conditions" refers to conditions that do not allow denaturation treatment that is normally used in the art for protein denaturation, for example, treatment using denaturing agents such as urea. In addition, such conditions do not allow changes in the compositions of original components of a biological sample such as serum or plasma, and changes in temperature, and the like. Specifically, the following treatments are avoided: addition of organic solvents; addition of surfactants and synthetic polymers with concentrations exceeding critical micelle concentrations; at least two-fold increase or decrease in the salt concentration; addition of oxidizing agents, reducing agents, and highly reactive reagents; at least 10-fold decrease in the protein concentration; removal of moisture (other than lyophilization); adjustment to pH 7 or less or 9 or more; stationary placement at −30° C. for many hours; and heating to 60° C. or higher. Those skilled in the art would understand specific conditions for allowing or not allowing protein denaturation, in addition to the above.

According to the method of the present invention, it is preferable to carry out inactivation treatment prior to protease treatment as a step of inhibiting endogenous protease activity that may slightly influence detection results and improving detection effects regarding a protein of interest. It is possible to perform inactivation by, for example, heating treatment at 56° C. for 30 to 40 minutes. Those skilled in the art can easily determine conditions for inactivation.

According to the method of the present invention, a protease is directly added to the obtained serum or plasma sample. The expression "directly added" used herein means that a protease with a minimum necessary solution composition is added to a sample containing proteins, i.e., the obtained serum or plasma sample, without protein denaturation treatment. For example, a protease to be added is adjusted to a high concentration of 10 mg/mL or higher using ultra-pure water or hydrochloric acid with a concentration of 1 mmol/L or lower. The protease is then directly added to a serum or plasma sample so that the volume of the protease is about one-fiftieth (1/50th) of that of the sample, thereby allowing initiation of a digestion reaction without substantially changing the original composition of the sample. The pH of the serum or plasma is initially maintained at pH 7.40 through buffering with bicarbonate ions. Therefore, the reaction environment is already suitable for many proteases, including trypsin, without the need to adjust pH using a different buffer solution. However, if particularly necessary, pH may be adjusted to pH 7 to 9 and more preferably pH 7.4 to 7.8. Those skilled in the art would be able to adequately determine conditions for pH adjustment, and a particularly preferable condition is buffering with sodium phosphate.

Examples of the "protease" suitably used in the present invention preferably include trypsin, lysyl endopeptidase, endopeptidase Asp-N, V8 protease, and metallo-endopeptidase Lys-N, with trypsin being particularly preferable. Trypsin has high substrate specificity, and the C-terminus of a peptide cleaved therewith is Lys or Arg, allowing the charge amount and charge localization of the peptide to be uniform. This is particularly preferable for preparation of samples for mass spectrometry.

The amount of a protease to be added to a sample may vary depending on conditions such as the types of protease and sample to be used, temperature, and treatment time.

However, it is preferably 1 to 50 µg and more preferably 20 to 40 with respect to 100 µL of the serum or plasma sample. In one embodiment of the method of the present invention, approximately 20 µg of trypsin is added to 100 µL of serum.

Protease treatment may be carried out at the reaction temperature of 0° C. to 40° C. and preferably 4° C. to 37° C. The treatment time for the protease treatment may be 1 to 24 hours, preferably 3 to 16 hours, and more preferably 8 to 12 hours. Those skilled in the art, however, may appropriately change or select such conditions. In addition, although not particularly limited, protease may be in the form of a solution or suspension that has been adjusted to have a high concentration as described above. After digestion, the protease can be readily removed in the step of separating proteins. In addition, it is also possible to use the protease as an immobilized enzyme bound to a solid support and apply the sample to the immobilized enzyme. Methods of preparing an immobilized enzyme are well known in the art. Examples of supports include, but are not particularly limited to, agarose, sepharose, polyacrylamide, polyethylene glycol, polystyrene, polyethylene, polypropylene, polyester, polyacrylonitrile, (meth)acrylic acid ester polymer, fluorine resin, metal complex resin, glass, metal, and magnetic material. The immobilized enzyme can also be removed in the step of separating proteins.

Surprisingly, it was discovered that when a serum or plasma sample was treated under the above conditions, albumin, globulin, and transferrin, which are present at high concentrations in serum or plasma, were not digested, and the results of mass spectrometry of the obtained peptides demonstrated that the mass spectra did not have peaks derived from these proteins. In particular, albumin, which accounts for 50% or more of the protein composition, was not digested. Therefore, it becomes possible to detect trace peptides that have been difficult to detect by conventional methods, thereby allowing very convenient and quick detection of a protein or peptide of interest in a sample.

The expressions "not digested" and "undigested" used for a certain protein mean that 90% or more, preferably 95% or more, more preferably 98% or more, and even more preferably 99% or more of the protein present in a sample is not digested by a protease added and remains intact. In other words, when serum or plasma is used as a sample, the digestion of a protein that is an impurity present in abundance in the sample, and especially the digestion of albumin, which is contained in a large amount in a sample, by a protease is less than 10%, preferably less than 5%, more preferably less than 2%, and even more preferably less than 1%. Most preferably, albumin is not digested at all by a protease according to the method of the present invention. Undigested proteins are removed in the subsequent step of separating peptides from proteins in the method of the present invention.

The expression "undigested protein" refers to a protein that is prevented from interacting with a protease and thus is not digested under the conditions of the present invention, because its tertiary structure and quaternary structure are highly folded, and/or the protein is bound to other protein(s) in a sample, for example. The method of the present invention is designed to preferentially allow digestion of proteins other than proteins having the above features so as to reverse the original concentration ratio in digested peptides.

Meanwhile, it is known that a protein called "α2 macroglobulin (A2M)" is present in serum or plasma. A2M is a protease inhibitor that functions to immobilize a variety of different proteases inside the cage-like A2M molecule, and it is contained in serum at a concentration of about 1 to 2 mg/mL. It is also known that a protease immobilized inside A2M maintains its activity, and it continues to digest molecules with low molecular weights that can access the internal portion of A2M (Sottrup-Jensen, L., J Biol Chem 1989, 264 (20), 11539-42). Although not limited to any theory, some proteins that are preferentially digested under the conditions of the method of the present invention are considered to be digested via A2M molecules in blood. That is, it is considered that a protease added to a sample such as serum reacts with A2M in the sample, thereby acting on proteins in the sample in the form of being covalently bound inside A2M. Accordingly, it may be preferable for a protein to be analyzed to have a molecular weight of approximately 10 kDa or less, according to the present invention. In addition, when a protein is digested according to the method of the present invention, among all peptides that can be formed as a result of protein digestion, only some peptides might be detected with high sensitivity. This phenomenon probably reflects the situation in which the protease inside A2M acts to partially digest a protein of interest in a selective manner.

In addition, the concentration of a protein to be detected in a sample depends on the sensitivity of the assay system. However, a concentration of 1 µg/mL or higher, and in particular, of 5 to 100 µg/mL, is advantageous for detection according to the method of the present invention. More specifically, the amount of a peptide to be actually detected may be 10 to 10,000 fmol. When 0.1 µL of a sample containing 5 µg/mL protein is subjected to MS assay, the amount of a peptide to be detected is approximately 15 fmol.

In the method of the present invention, undigested proteins are separated from peptides by making use of differences in the properties between the proteins and digested peptides. For this purpose, for example, a process of adding an organic solvent or acid to cause proteins to precipitate and collecting the centrifugal supernatant thereof, a process of performing ultrafiltration or gel filtration to obtain a high-molecular-weight protein fraction and a low-molecular-weight peptide fraction, a process of allowing proteins to selectively bind to a support by making use of the strong hydrophobic interaction of the proteins, or the like can be employed. This process is carried out after reaction with a protease so that proteins that are originally contained at high concentrations in a serum or plasma sample and are resistant to protease digestion can be removed from the sample, thereby enabling mass spectrometry of the sample containing peptides from trace proteins.

As described above, by pretreating a serum or plasma sample by the method of the present invention and assaying the obtained peptides using a mass spectrometer, it is possible to detect trace proteins in a sample in a convenient and high-throughput manner without causing proteins that are present in abundance in the sample, such as albumin, to disturb detection.

Mass spectrometry can be performed by applying peptides ionized by MALDI, ESI, or the like to a double-focusing-type, quadrupole-type, time-of-flight (TOF)-type, or Fourier transform ion cyclotoron resonance-type analytical device. Furthermore, mass spectrometry may also be performed by liquid chromatography-mass spectrometry (LC/MS) combined with high performance liquid chromatography. Mass spectrometry can be performed by multiple reaction monitoring (MRM) using a triple quadrupole mass spectrometer in an LC/MS system that is widely used in the art for quantitative detection of peptides. MRM assay can be carried out using, for example, LCMS-8080 (Shimadzu Corporation). MALDI-TOF MS assay can be carried out using, for example, AXIMA-Resonance (Shimadzu Corporation).

Tandem MS (MS/MS) analysis that is used for detailed and accurate analysis is employed to select and further subject to mass analysis a precursor ion from a peptide of interest, thereby allowing the identification and quantitative determination of the peptide with the use of the generated product ions. Based on the obtained analysis results, the peptide of interest can be confirmed with reference to peak information obtained in the same manner using a control sample or information in an existing database, and the amino acid sequence of the peptide can be determined. MS/MS assay can be performed by, for example, AXIMA-Resonance (Shimadzu Corporation).

In the method of the present invention, more specifically, a peptide to be actually analyzed by mass spectrometry is first selected for a protein to be detected.

The amino acid sequence information of a protein can be obtained from, for example, http://www.uniprot.org/. Types of peptides that may be generated as a result of protease digestion of a protein can be predicted on, for example, http://web.expasy.org/peptide_mass/. Data on mass spectrometry results of peptides that have been generated via protease digestion can be queried on, for example, http://peptide.nist.gov/.

For example, with regard to the selection of peptides that may be subjected to mass spectrometry after digestion with trypsin, some exclusion criteria are known concerning the amino acid sequences of such peptides (Nat. Biotechnol. 2009, 27 (2), 190-8). Specifically, for example, it is essentially required that a plurality of proteins do not contain any identical sequences in order to ensure the reliability of detection results. For example, it is preferable that: the peptide is not a hydrophilic peptide of less than 8 amino acids or a hydrophobic peptide of more than 20 amino acids; there are no basic amino acids adjacent to each other (KK, RR, KR, RK) at the carboxy-terminus as a result of trypsin digestion; and it does not contain a cysteine residue, a methionine residue, or an N-terminal glutamine or asparagine. Preferable peptides used as markers for detection via mass spectrometry can be computer-predicted based on the above information. Those skilled in the art can arbitrarily select peptides used for quantitative determination from the above peptides.

In one embodiment, when Annexin A4 (SEQ ID NO: 1), which is known to be highly expressed in some ovarian cancer, is designated as a peptide to be detected from blood, and peptides that meet the following conditions are considered to be preferable peptide candidates:
(Condition 1): the amino acid sequence of the peptide is not present in other proteins;
(Condition 2): the sequence does not contain cysteine;
(Condition 3) the sequence has 8 to 20 amino acids; and
(Condition 4) the amino acid at the N-terminus of the sequence is not glutamine or asparagine, the following peptides can be selected.

AASGFNAMEDAQTLR (SEQ ID NO: 2, corresponding to amino acid numbers 10-24 of the amino acid sequence of SEQ ID NO: 1);

GLGTDEDAIISVLAYR (SEQ ID NO: 3, corresponding to amino acid numbers 29-44 of the amino acid sequence of SEQ ID NO: 1);

ISQTYQQQYGR (SEQ ID NO: 4, corresponding to amino acid numbers 124-134 of the amino acid sequence of SEQ ID NO: 1);

SDTSFMFQR (SEQ ID NO: 5, corresponding to amino acid numbers 142-150 of the amino acid sequence of SEQ ID NO: 1);

VLVSLSAGGR (SEQ ID NO: 6, corresponding to amino acid numbers 151-160 of the amino acid sequence of SEQ ID NO: 1);

DEGNYLDDALVR (SEQ ID NO: 7, corresponding to amino acid numbers 161-172 of the amino acid sequence of SEQ ID NO: 1);

SETSGSFEDALLAIVK (SEQ ID NO: 8, corresponding to amino acid numbers 226-241 of the amino acid sequence of SEQ ID NO: 1);

GLGTDDNTLIR (SEQ ID NO: 9, corresponding to amino acid numbers 260-270 of the amino acid sequence of SEQ ID NO: 1);

AEIDMLDIR (SEQ ID NO: 10, corresponding to amino acid numbers 276-284 of the amino acid sequence of SEQ ID NO: 1);

GDTSGDYR (SEQ ID NO: 11, corresponding to amino acid numbers 301-308 of the amino acid sequence of SEQ ID NO: 1).

In some cases, computer-predicted peptides may not be susceptible to digestion with a protease due to conditions such as their positions in the protein conformation. In particular, for a protein undergoing digestion via A2M, it is preferable to select, as analytes, peptides at positions susceptible to digestion in the presence of A2M. Further, there may be a case in which it is not possible to distinguish between different peptides having the same mass and happening to coexist. Therefore, for the realization of detection of certain proteins for clinical applications with the applied use of the method of the invention, it is necessary to investigate whether a predicted peptide is a suitable marker and select the optimal peptide from candidate peptides. Particularly preferable peptides for detection of Annexin A4 according to the method of the present invention are peptides having the amino acid sequences of SEQ ID NOS: 2, 3, and 7.

EXAMPLES

The present invention is further described with reference to the Examples below. However, the present invention is not limited to these Examples.

Example 1

[Selection of Peptides to be Analyzed]

Annexin A4 (ANXA4) (SEQ ID NO: 1), which is contained in a trace amount in serum and expected to serve as an ovarian cancer biomarker, was subjected to semi-quantitative detection according to the present invention.

DEGNYLDDALVR (SEQ ID NO: 7) was selected as a peptide appropriate for the present invention in accordance with the conditions described in Expert Rev. Proteomics 2004, 1 (4), 503-12; and Nat. Biotechnol. 2009, 27 (2), 190-8.

[Preparation of Samples and Protease]

A purified recombinant protein (ANXA4) that had been obtained from the E. coli expression system was added at a concentration of 3 mg/mL to commercially available human serum (product code 14-402E, Lonza Japan) so that it accounted for 10% of the final volume. The resulting mixture was serially diluted with the serum to prepare samples containing ANXA4 at concentrations of 300, 150, 75, 38, 19, 9, and 5 µg/mL, respectively. The serum samples were inactivated by heat treatment at 56° C. for 40 minutes and further clarified using a 0.44-μm filter (Ultrafree, Millipore). Powdered trypsin (product code: 203-09893, Wako Pure Chemical Industries, Ltd.) was dissolved in a 1 mmol/L hydrochloric acid solution to obtain a trypsin solution at a concentration of 10 mg/mL.

[Pretreatment by the Present Invention]

The pretreatment step of the present invention is described below. The serum samples (100 μL each) prepared above were introduced into 1.5-mL Eppendorf tubes, and 2 μL of a trypsin solution was added, followed by reaction at 37° C. for 16 hours (about 20 μg of trypsin was added to 100 μL of each serum sample). After the reaction, the samples were transferred to the top of the ultrafiltration filter (Amicon 10,000 MWCO filter, Millipore), followed by centrifugation at 10,000 g for 60 minutes. The filtrate of each sample that transferred through the filter to the lower part was directly used as a sample for mass spectrometry.

[Pretreatment by the Conventional Method]

A step of preparing trypsin-digested peptides from serum according to the conventional method is described below. Urea powder was weighed to 10 mg and introduced into 1.5-mL Eppendorf tube, and the serum samples prepared above (10 μL each) were added (denaturation). After mixing, 2 μL of 50 mmol/L Tris(2-carboxyethyl)phosphine hydrochloride was added and allowed to react at 37° C. for 30 minutes (reduction). Next, 0.8 μL, of a liquid mixture of 0.5 mol/L iodoacetamide and 1 mol/L ammonium bicarbonate was added and allowed to react at ordinary temperature for 45 minutes (alkylation). The reaction mixture was diluted with 160 μL of 10 mmol/L Tris-hydrochloric acid buffer (pH 8.0) and 2 μL of the above trypsin solution was added, followed by reaction at 37° C. for 16 hours (about 20 μg of trypsin was added to 10 μL of each serum sample). After the reaction, 4 μL of 10% trifluoroacetic acid was added to the peptide solutions to obtain samples for mass spectrometry.

[MALDI MS Assay]

The samples (0.5 μL each) obtained above were desalted using ZipTip (trademark, Millipore). Upon desalting, each sample was diluted with 10 μL of 0.1% trifluoroacetic acid containing 1 nmol/mL of a reference peptide (amino acid sequence: PPPPPPPPPPPPPPR (SEQ ID NO: 12), hereinafter referred to as "P14R"). One-tenth (1/10th) by the volume of each eluate was spotted on a μFocusing plate (Shimadzu GLC). After air drying, 1 μL of 3 mg/mL 2,5-dihydroxybenzoic acid was spotted as a matrix. After crystallization, assay was conducted using MALDI MS (AXIMA-Resonance, Shimadzu Corporation). Profiles (200 in total) were obtained at 200 spots by driving raster scanning at a laser intensity of 100 in the positive mid mass mode and accumulated to obtain a mass spectrum from each spot.

[MS/MS Assay]

For MS/MS assay, after setting an ion trap for the monoisotopic mass of a subject, profiles (200 in total) were obtained at 200 spots by driving raster scanning at a laser intensity of 110 in the positive mid mass mode and accumulated. The setting value of CID (Collision Induced Dissociation) intensity was appropriately adjusted to the subject.

[Method of Data Processing]

The intensity of the signal derived from P14R (m/z 1533.9) and the intensity of the signal derived from ANXA4 (a peptide having the amino acid sequence of SEQ ID NO: 7) (m/z 1379.6) were calculated through a process involving extraction from the mass spectra. In addition, based on the product ion spectrum from m/z 1379.6 obtained in the MS/MS mode, the intensity of the product ion at m/z 458.3 was also calculated through a process involving extraction.

The signal intensity in the MS mode was normalized relative to m/z 1533 (P14R), and the increase or decrease of the signal intensity due to ionization was corrected.

[Results]

FIG. 1 shows the mass spectra of the digested serum peptides obtained by pretreatment according to the method of the present invention or the conventional method. The asterisks (*) denote albumin-derived peaks among the observed peaks. As a result of comparison, almost all of the major peaks observed in the upper spectrum of the conventional method were albumin-derived peaks, while the lower spectrum of the method according to the present invention exhibited inhibited generation of albumin-derived peaks.

Figure 2:
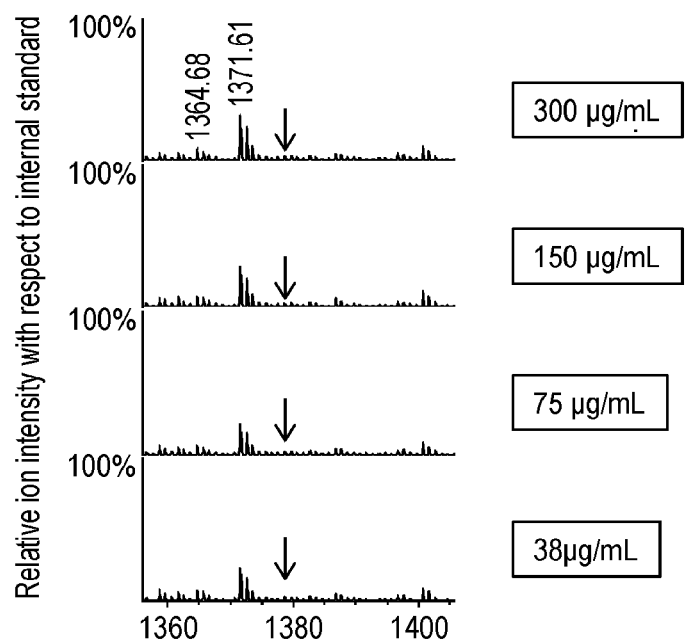
FIG. 2 shows enlarged mass spectra around m/z 1379 for digested serum peptides obtained from serum samples having Annexin A4 (ANXA4) spiking concentrations of 300, 150, 75, and 38 μg/mL. Each arrow represents an ANXA4-derived peptide (A: the conventional method; B: the method of the present invention).
Figure 2:
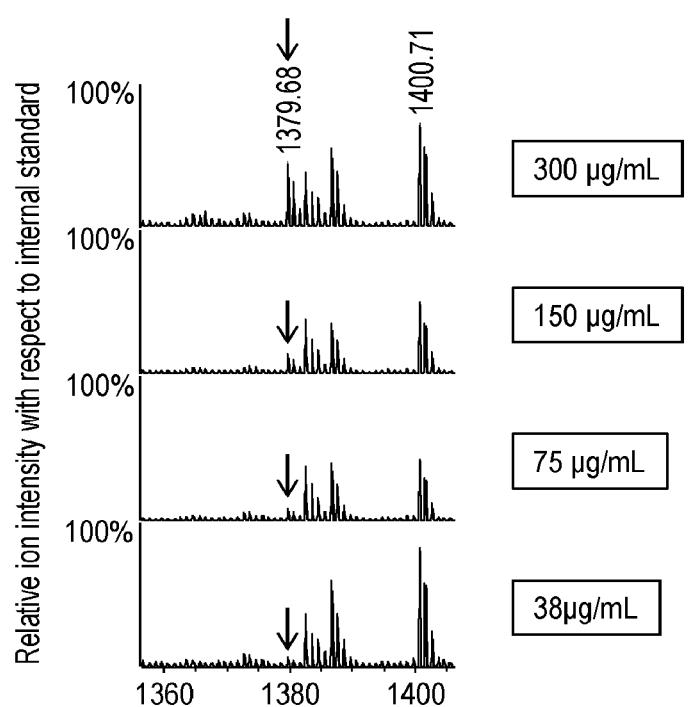

FIG. 2 shows enlarged mass spectra around the peak of m/z 1379.6. As shown with arrows, a peak that was not detected after pretreatment of the conventional method (A) was detected after pretreatment of the present invention (B) at concentrations of 38 μg/ml or higher. As is apparent from these results, although no ANXA4-derived peaks were detected with the conventional method, the peaks were observed in a concentration-dependent manner with the method of the present invention.

Figure 3A:
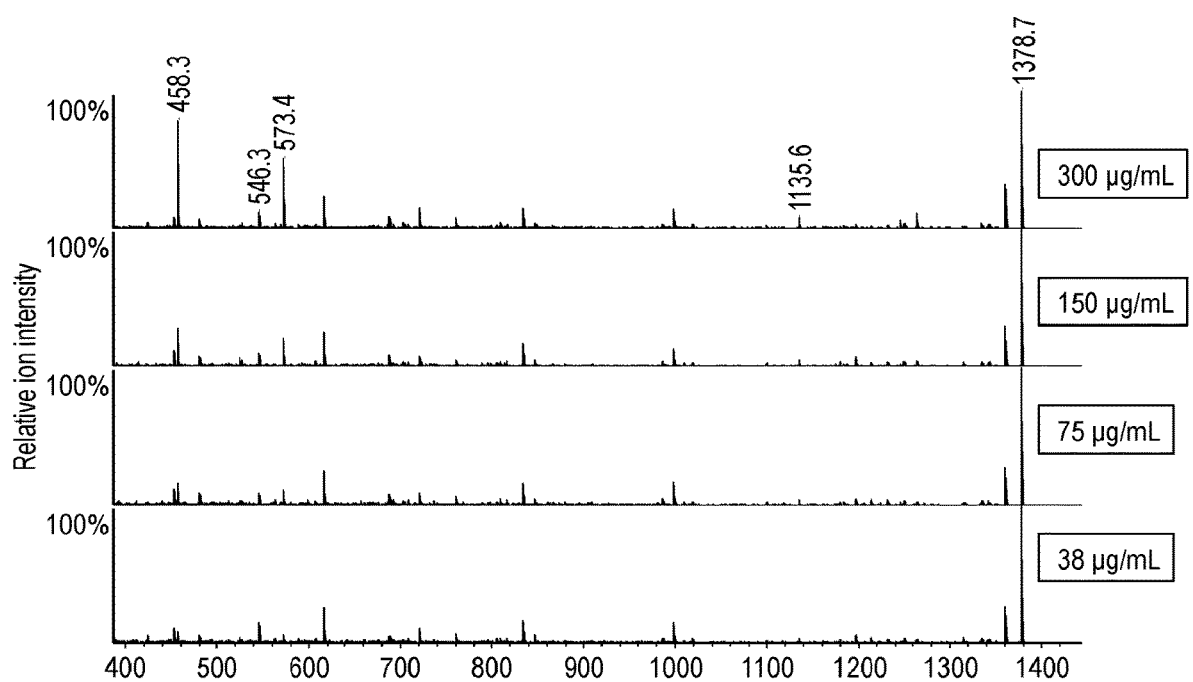
FIG. 3A shows product ion spectra obtained by MS/MS assay of the peak at m/z 1379.6 for spots of digested serum peptides obtained by the conventional method from serum samples having ANXA4 spiking concentrations of 300, 150, 75, and 38 μg/mL.
Figure 3B:
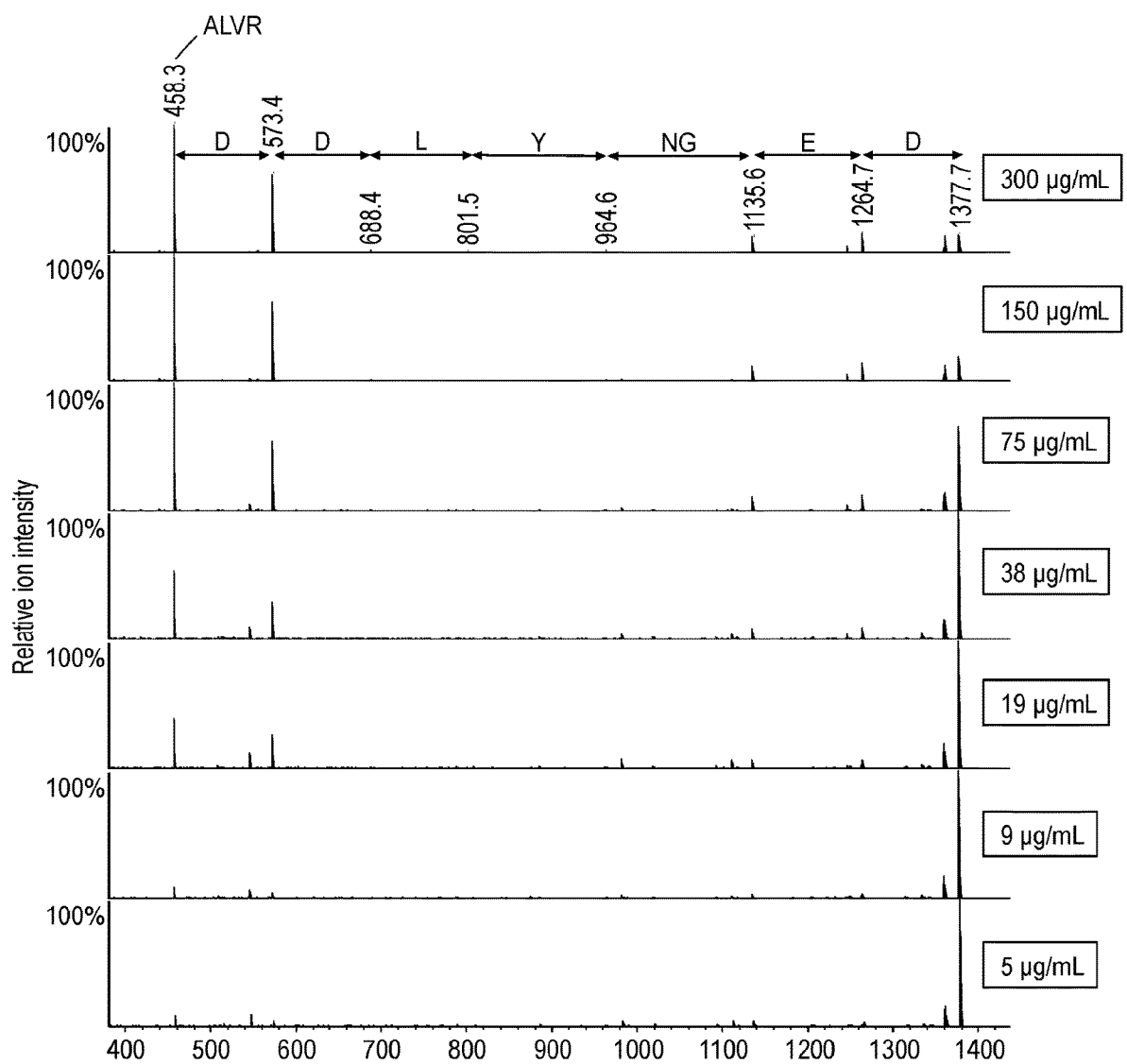
FIG. 3B shows product ion spectra obtained by MS/MS assay of the peak at m/z 1379.6 for spots of digested serum peptides obtained by the method of the present invention from serum samples having ANXA4 spiking concentrations of 300, 150, 75, 38, 19, 9, and 5 μg/mL.

The above peak (m/z 1379.6) was selected for a precursor ion, and the product ion spectrum was obtained through MS/MS assay. The results are shown in FIG. 3. The results of FIG. 3 showed that the peak at m/z 1379.6 represented an ANXA4-derived peptide (SEQ ID NO: 7). This was also confirmed by the fact that the spectrum was identical to the spectrum obtained by directly analyzing ANXA4 without the addition to samples.

Further, according to the conventional method (FIG. 3A), detection was possible at serum ANXA4 concentrations of 75 μg/mL or higher, while detection was possible even at low concentrations of 5 μg/mL according to the method of the present invention (FIG. 3B), and the detection sensitivity was improved by more than 10 times. Moreover, many signals other than ANXA4-derived signals coexisted in the case of the conventional method, while ANXA4-derived signals were exclusively detected in the case of the method of the invention, and a favorable S/N ratio was obtained.

Table 1 below summarizes the detection of the ANXA4-derived peptides through the method of the present invention and the conventional method based on the results obtained above. Regarding the corrected ANXA4-drived signal intensity, the conventional method involving denaturation was compared with the direct digestion method of the present invention. As a result, it was found that detection efficiency was significantly improved in both MS data and MS/MS data. That is, whereas the ANXA4-derived peak at m/z 1379 could not be quantitatively detected by the conventional method, the peak was detected in a concentration-dependent manner according to the method of the present invention.

TABLE 1

Table 1 shows the intensities of ANXA4-derived signals detected for serum samples at different spiking concentrations via MS and MS/MS. The corrected ANXA4-derived signal intensity (Normalized ANXA4) was obtained by dividing the signal intensity at m/z 1379.6 by that at m/z 1533.9.

| Pre-treatment | ANXA4 concentration (μg/mL) | MS m/z 1533.9 Intensity | m/z 1379.6 Intensity | ANXA4 Corrected intensity | MS/MS m/z 458.3 Intensity |
|---|---|---|---|---|---|
| Conventional method | 300 | 33344 | 1174 | 0.035 | 3385 |
| | 150 | 38984 | 1177 | 0.030 | 1483 |
| | 75 | 46718 | 1138 | 0.024 | 858 |
| | 38 | 33905 | 968 | 0.029 | 426 |

TABLE 1-continued

Table 1 shows the intensities of ANXA4-derived signals detected for serum samples at different spiking concentrations via MS and MS/MS. The corrected ANXA4-derived signal intensity (Normalized ANXA4) was obtained by dividing the signal intensity at m/z 1379.6 by that at m/z 1533.9.

| Pre-treatment | ANXA4 concentration (µg/mL) | MS m/z 1533.9 Intensity | m/z 1379.6 Intensity | ANXA4 Corrected intensity | MS/MS m/z 458.3 Intensity |
|---|---|---|---|---|---|
| Method of the present invention | 300 | 25250 | 6245 | 0.247 | 61307 |
| | 150 | 23817 | 3129 | 0.131 | 45703 |
| | 75 | 22657 | 1438 | 0.063 | 10201 |
| | 38 | 21526 | 959 | 0.045 | 2398 |
| | 19 | 20915 | 841 | 0.040 | 2124 |
| | 9 | 27242 | 519 | 0.019 | 882 |
| | 5 | 31950 | 565 | 0.018 | 618 |

Example 2

[Selection of Peptides to be Analyzed]

The above peptides of SEQ ID NOS: 2-11 are preferable peptide candidates for the method of the present invention. In order to select particularly preferable peptides from these peptides, a preliminary experiment was carried out using α2 macroglobulin (A2M).

A2M protein (product code M6159, Sigma-Aldrich) and purified recombinant protein ANXA4 obtained using an *E. coli* expression system were adjusted to concentrations of 2 mg/mL and 3 mg/mL, respectively, with the use of phosphate-buffered saline (PBS). Powdered trypsin (product code: 203-09893, Wako Pure Chemical Industries, Ltd.) was dissolved in a 1 mmol/L hydrochloric acid solution to obtain a trypsin solution at a concentration of 10 mg/mL.

The A2M solution (7.5 µL) and the ANXA4 solution (2 µL) were mixed and PBS (10 µL) was added to the mixture, followed by heating at 56° C. for 30 minutes. Then, 0.5 µL of the trypsin solution was added, followed by digestion at 4° C. for 12 hours. A control was prepared for comparison by replacing the A2M solution by PBS, followed by the same treatment. Peptides obtained after digestion were desalted using ZipTip (trademark, Millipore). Each eluate was spotted on µFocusing plate (Shimadzu GLC). After air drying, 1 µL of 3 mg/mL 2,5-dihydroxybenzoic acid was spotted as a matrix. After crystallization, assay was conducted using MALDI MS (AXIMA-Resonance, Shimadzu Corporation).

Figure 4:
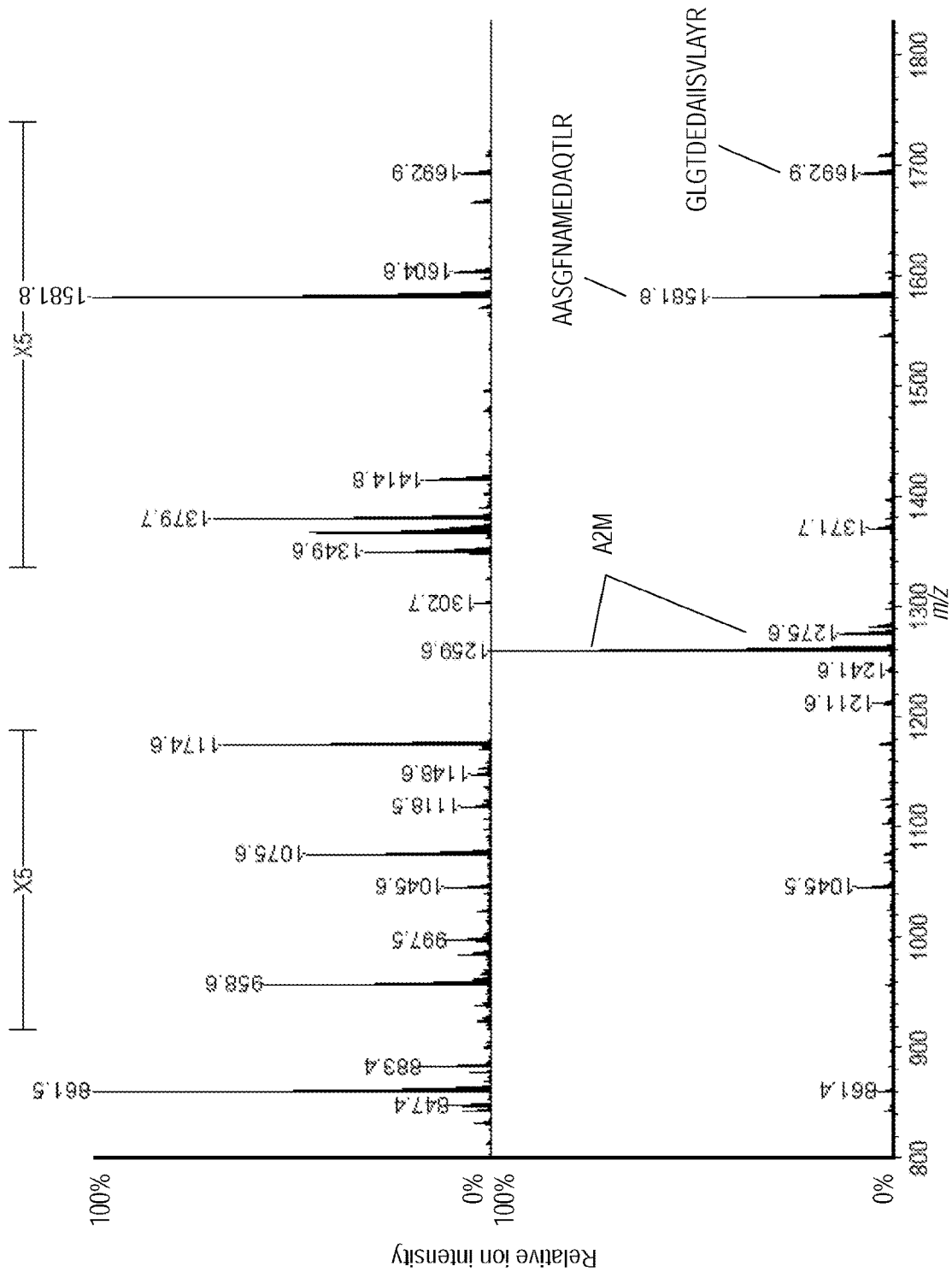
FIG. 4 shows mass spectra of the peptides obtained by subjecting AnnexinA4 (ANXA4) to trypsin digestion. The upper spectrum represents the results of trypsin digestion of ANXA4 alone. The lower spectrum represents the results of digestion of ANXA4 that was mixed with α2 macroglobulin and heated in advance.

FIG. 4 shows mass spectra of ANXA4-derived digested peptides in the presence and in the absence of A2M (final concentration: 0.75 mg/mL). Results of the comparison of the obtained mass spectra showed that various peptide species were detected with high signal intensities as a result of digestion in the absence of A2M with the addition of ANXA4 alone (upper spectrum), while peaks of the AASGFNAMEDAQTLR peptide (m/z 1581.7, SEQ ID NO: 2) and the GLGTDEDAIISVLAYR peptide (m/z 1682.9, SEQ ID NO: 3) were clearly observed in the presence of A2M (lower spectrum), indicating that these peptides were selectively detected. Accordingly, it is expected that these peptides can be detected from serum samples with high sensitivity by the method of the present invention.

AASGFNAMEDAQTLR (SEQ ID NO: 2), which has been found to be detected with remarkably good sensitivity, was selected as a peptide to be analyzed in the following Examples.

Example 3

[Preparation of Samples and Protease]

Preparation was carried out in the same manner as Example 1.

[Pretreatment by the Present Invention]

Pretreatment was carried out in the same manner as Example 1, except that trypsin digestion was carried out at 4° C. for 16 hours.

[Pretreatment by the Conventional Method]

Pretreatment was carried out in the same manner as Example 1.

[MALDI MS Assay]

The samples (0.5 µL each) obtained above were desalted using ZipTip.

Standard peptide P14R (10 pmol) was added to each eluate. One-tenth (1/10th) by the volume of each eluate was spotted on a µFocusing plate (Shimadzu GLC). After air drying, 1 µL of 3 mg/mL 2,5-dihydroxybenzoic acid was spotted as a matrix. After crystallization, assay was conducted using MALDI MS (AXIMA-Resonance, Shimadzu Corporation). Profiles (200 in total) were obtained at 200 spots by driving raster scanning at a laser intensity of 100 in the positive mid mass mode and accumulated to obtain a mass spectrum from each spot.

[MS/MS Assay]

MS/MS assay was carried out in the same manner as Example 1.

[Method of Data Processing]

The intensity of the signal derived from P14R (m/z 1533.9) and the intensity of the signal derived from ANXA4 (a peptide having the amino acid sequence of SEQ ID NO: 2) (m/z 1581.7) were calculated through a process involving extraction from the mass spectra, by detecting peaks with the signal intensity of 0.5 mV as a threshold. In addition, based on the product ion spectrum from m/z 1581.7 obtained in the MS/MS mode, the intensity of the product ion at m/z 588.3 (corresponding to y5 ion of SEQ ID NO: 2) was also calculated through a process involving extraction. Signals that were not recognized upon detection of peaks with the threshold of 0.5 mV were designated as "Not detected" (ND). The signal intensity in the MS mode was normalized relative to m/z 1533 (P14R), and the increase or decrease of the signal intensity due to ionization was corrected.

[Results]

Figure 5A:
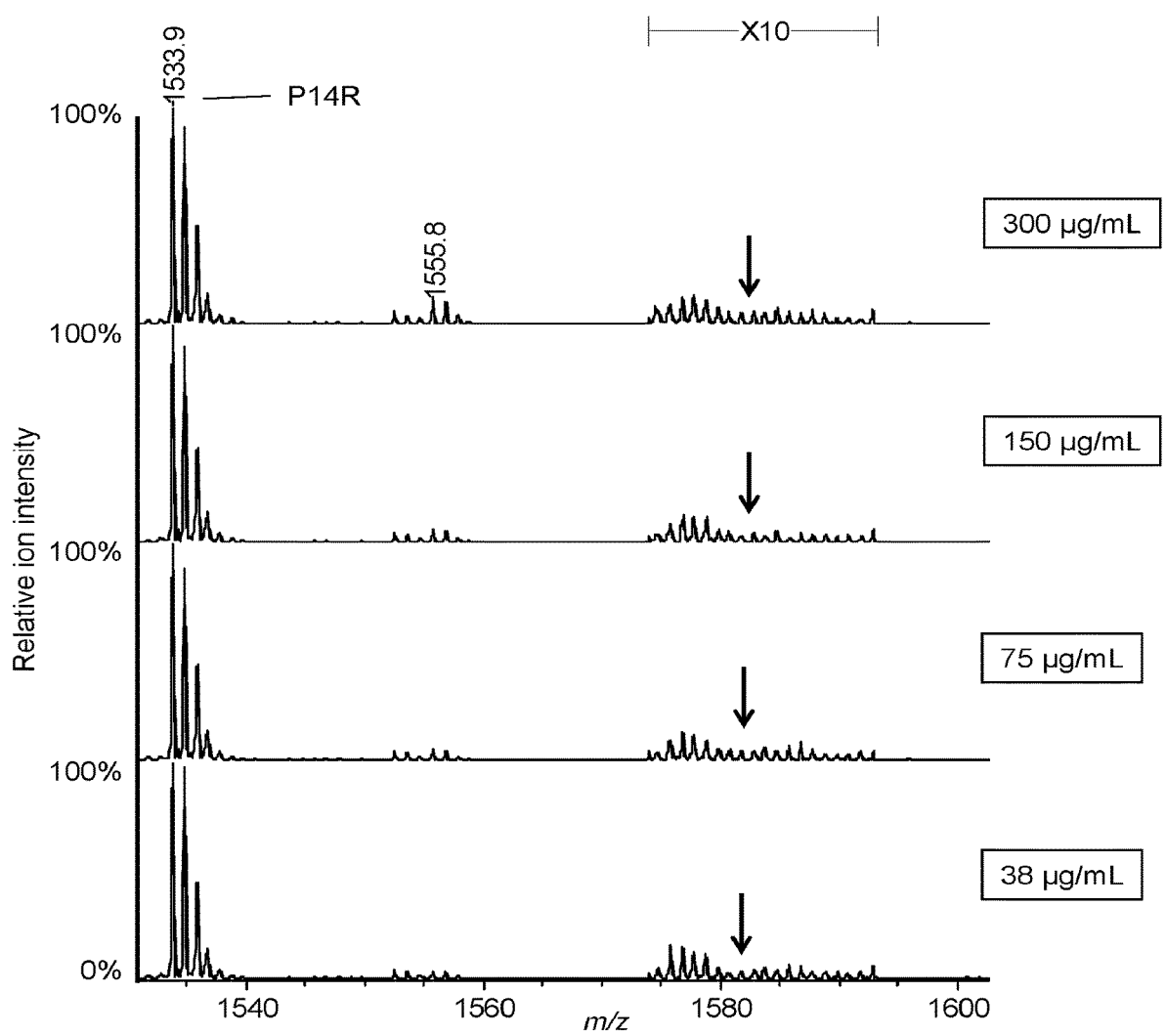
FIG. 5A shows enlarged mass spectra around m/z 1581 for digested serum peptides obtained by the conventional method from serum samples having Annexin A4 (ANXA4) spiking concentrations of 300, 150, 75, and 38 µg/mL. Each arrow represents an ANXA4-derived peptide.
Figure 5B:
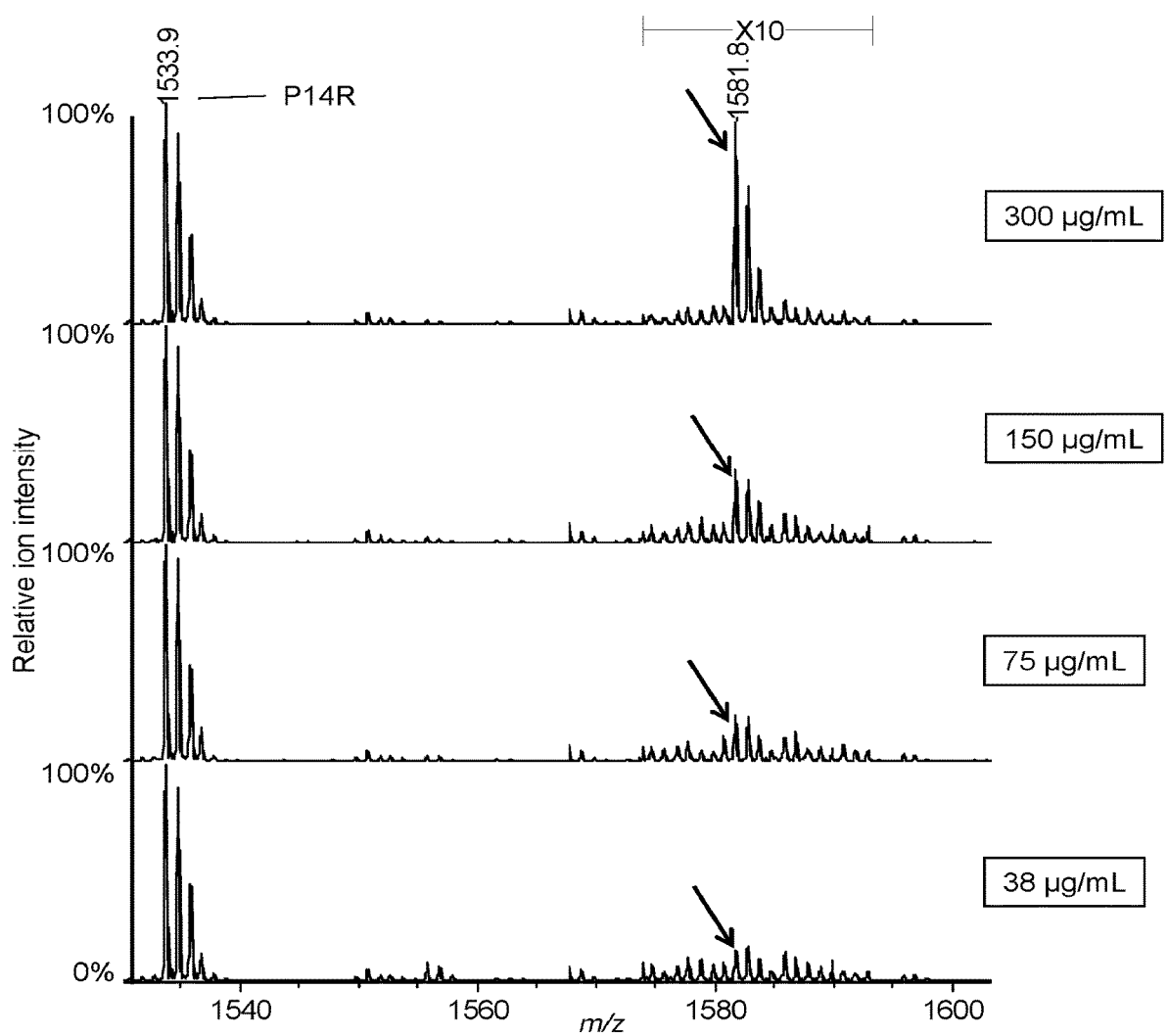
FIG. 5B shows enlarged mass spectra around m/z 1581 for digested serum peptides obtained by the method of the present invention from serum samples having Annexin A4 (ANXA4) spiking concentrations of 300, 150, 75, and 38 µg/mL. Each arrow represents an ANXA4-derived peptide.

FIG. 5 shows enlarged mass spectra around the peak of m/z 1581.7. As shown with arrows, a peak that was not detected after pretreatment of the conventional method (A) was detected after pretreatment of the present invention (B) at concentrations of 38 µg/ml or higher. As is apparent from these results, although no ANXA4-derived peaks were detected with the conventional method, the peaks were observed in a concentration-dependent manner with the method of the present invention. Under the above experimental conditions, among candidate ANXA4-derived peptides (SEQ ID NOS: 2-11), only the peptides of SEQ ID NOS: 2 and 3 were actually detected based on the mass spectra, and they were confirmed to be identical to the peptides that were regarded as preferable peptides in Example 2.

Figure 6A:
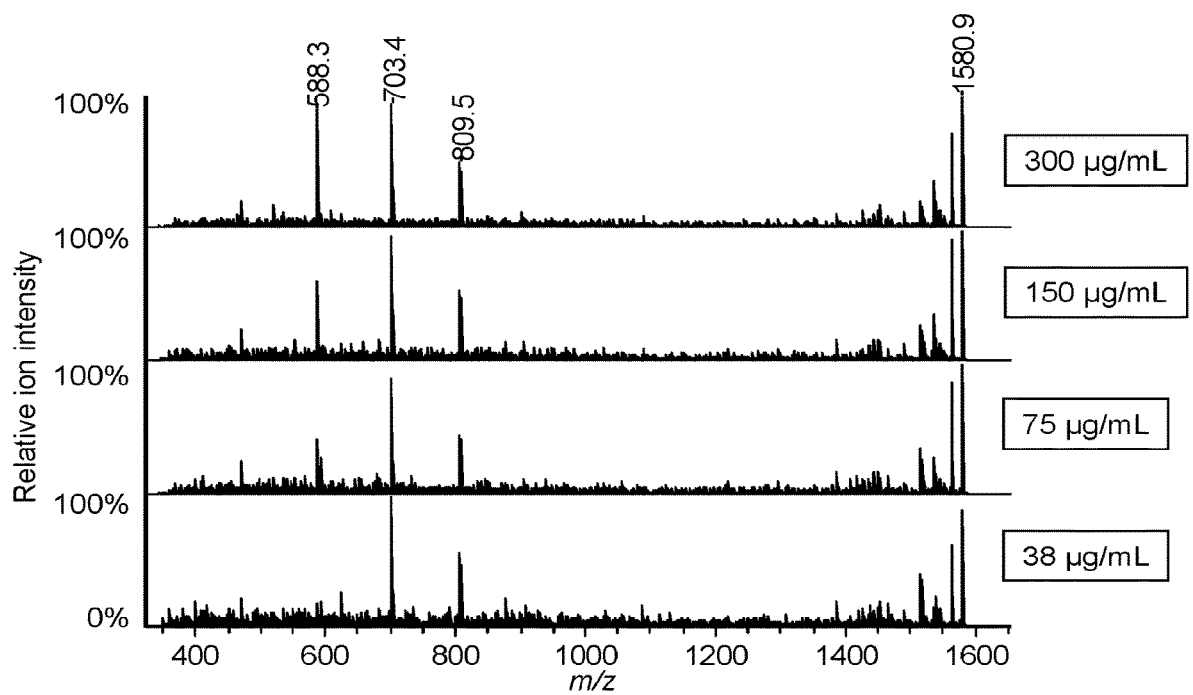
FIG. 6A shows product ion spectra obtained by MS/MS assay of the peak at m/z 1581.7 for spots of digested serum peptides obtained by the conventional method from serum samples having ANXA4 spiking concentrations of 300, 150, 75, and 38 µg/mL.
Figure 6B:
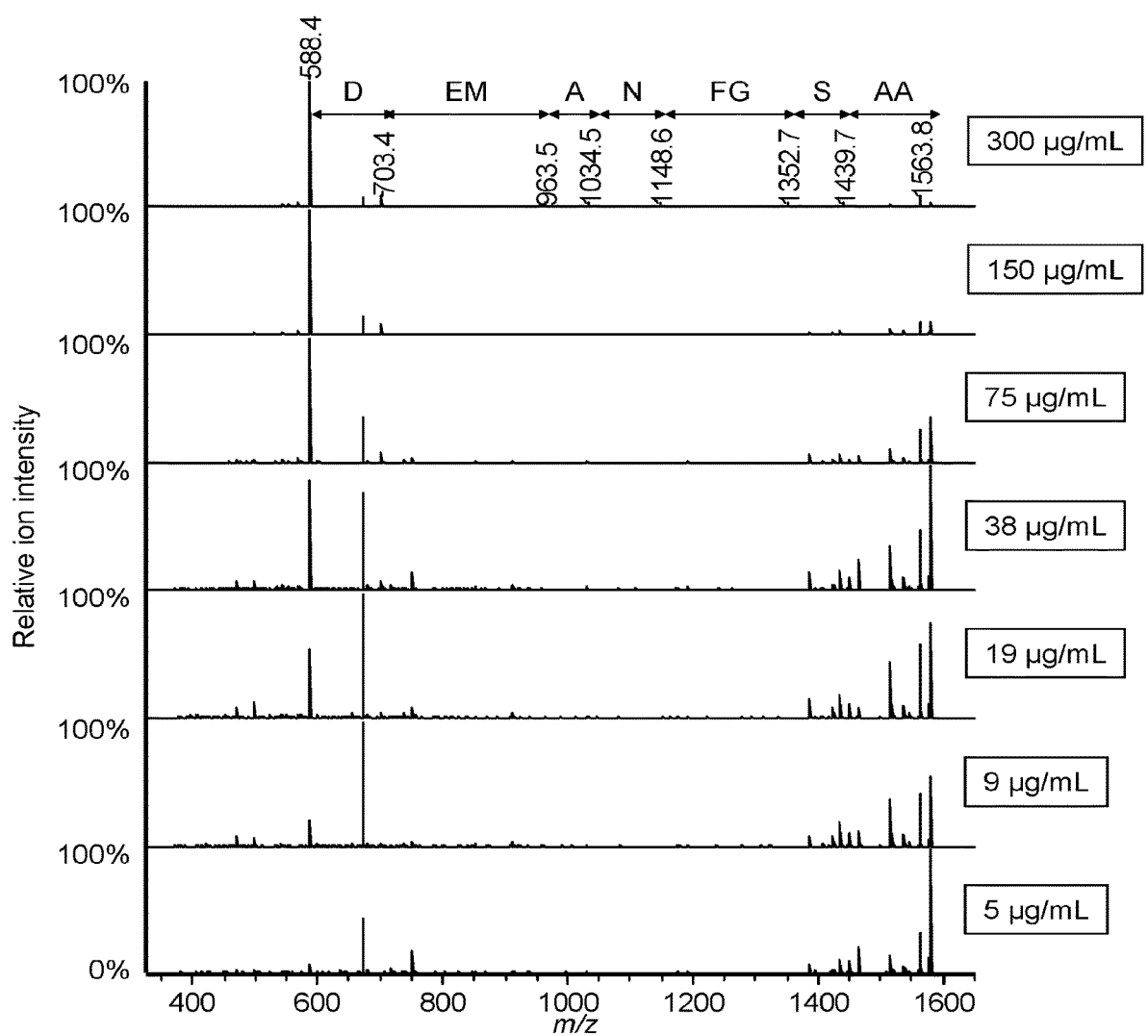
FIG. 6B shows product ion spectra obtained by MS/MS assay of the peak at m/z 1581.7 for spots of digested serum peptides obtained by the method of the present invention from serum samples having ANXA4 spiking concentrations of 300, 150, 75, 38, 19, 9, and 5 µg/mL.

The above peak (m/z 1581.7) was selected for a precursor ion, and the product ion spectrum was obtained through MS/MS assay. The results are shown in FIG. 6. The results of FIG. 6 showed that the peak at m/z 1581.7 represented an ANXA4-derived peptide (SEQ ID NO: 2). This was also confirmed by the fact that the spectrum was identical to the spectrum obtained by directly analyzing ANXA4 without the addition to samples.

Further, according to the conventional method (FIG. 6A), detection was possible at serum ANXA4 concentrations of 75 µg/mL or higher, while detection was possible even at low concentrations of 5 µg/mL according to the method of the present invention (FIG. 4B), and the detection sensitivity was improved by more than 10 times. Moreover, many signals other than ANXA4-derived signals coexisted in the case of the conventional method, while ANXA4-derived signals were exclusively detected in the case of the method of the invention, and a favorable S/N ratio was obtained.

Table 2 below summarizes the detection of the ANXA4-derived peptides through the method of the present invention and the conventional method, based on the results obtained above. Regarding the corrected ANXA4-drived signal intensity, the conventional method involving denaturation was compared with the direct digestion method of the present invention. As a result, it was found that detection efficiency was significantly improved in both MS data and MS/MS data. That is, whereas the ANXA4-derived peak at m/z 1581.7 could not be quantitatively detected by the conventional method, the peak was detected in a concentration-dependent manner by the method of the present invention.

TABLE 2

Table 2 shows the intensities of ANXA4-derived signals detected for serum samples at different spiking concentrations via MS and MS/MS. The corrected ANXA4-derived signal intensity (Normalized ANXA4) was obtained by dividing the signal intensity at m/z 1581.7 by that at m/z 1533.9.

| | ANXA4 | MS | | | |
|---|---|---|---|---|---|
| Pre-treatment | concen-tration (µg/mL) | m/z 1533.9 Intensity | m/z 1581.7 Intensity | ANXA4 Corrected intensity | MS/MS m/z 588.3 Intensity |
| Conven-tional method | 300 | 39049 | 215 | 0.006 | 1442 |
| | 150 | 38523 | 137 | 0.004 | 593 |
| | 75 | 33021 | 124 | 0.004 | 320 |
| | 38 | 25397 | 168 | 0.007 | ND |
| Method of the present invention | 300 | 29416 | 2492 | 0.085 | 41927 |
| | 150 | 25969 | 989 | 0.038 | 17462 |
| | 75 | 28783 | 515 | 0.018 | 10031 |
| | 38 | 29333 | 397 | 0.014 | 2820 |
| | 19 | 29187 | 298 | 0.010 | 1706 |
| | 9 | 15593 | 163 | 0.010 | 818 |
| | 5 | 15118 | 156 | 0.010 | 314 |

The above results suggest that the pretreatment method of the present invention is obviously effective for eliminating the influence of proteins such as albumin, which are present in abundance in blood, to obtain peptide signals derived from the protein of interest, thereby achieving convenient pretreatment for biomarker assay via mass spectrometry.

INDUSTRIAL APPLICABILITY

The present invention was created to provide a method of detecting and identifying blood proteins via LC/MS or MALDI-TOF MS. According to the present invention, a method for pretreating a blood sample that is useful for exploration of disease biomarkers and allows realization of clinical testing by biomarker assay using the mass spectrometers is provided.

All publications, patents, and patent applications cited herein are incorporated herein by reference in their entirety.

The invention claimed is:

1. A method of detecting a target protein in a serum or plasma sample via mass spectrometry, the method comprising:
   (a) directly adding a protease to the sample including albumin and the target protein under a temperature in a range of 4° C. to 37° C. and a pH in a range of 7 to 9, thereby digesting the target protein while the albumin is not digested to obtain a mixture containing the albumin and peptides derived from the target protein;
   (b) removing the albumin from the mixture of (a); and
   (c) subjecting the mixture after the removal of the albumin to mass spectrometry, wherein the method excludes immunoprecipitation and ion-exchange chromatography.

2. The method according to claim 1, wherein the protease is trypsin.

3. The method according to claim 1, wherein the protease is an immobilized enzyme.

4. The method according to claim 1, wherein α2 macroglobulin is present in the sample.

5. The method according to claim 1, wherein the mass spectrometry comprises LC/MS analysis or MALDI-TOF analysis.

6. The method according to claim 1, wherein the mass spectrometry comprises tandem mass spectrometry analysis.

7. The method according to claim 1, wherein the protease is at least one protease selected from the group consisting of trypsin, lysyl endopeptifase, endopeptidase Asp N, V8 protease and metallo-endopeptidase Lys-N.

8. The method according to claim 1, wherein the sample is not treated with surfactants or synthetic polymers with concentrations exceeding critical micelle concentrations prior to adding the protease.

9. The method according to claim 1, wherein the sample is not treated with an oxidizing agent or reducing agent prior to adding the protease.

10. The method according to claim 1, wherein a protein concentration of the sample is not increased prior to adding the protease.

11. The method according to claim 1, wherein moisture of the sample is not removed prior to adding the protease, other than lyophilization, prior to adding the protease.

12. The method according to claim 1, wherein the sample is not placed stationary at −30° C. for hours prior to adding the protease.

13. The method according to claim 1, wherein the sample is not heated to 60° C. or higher prior to adding the protease.

14. The method according to claim 1, wherein the protease is added without a buffer.

15. The method according to claim 1, wherein the protease is added without an ammonium bicarbonate solution or Tris buffer.

16. The method according to claim 1, wherein the proteins have a molecular weight of 10 kDa or less.

17. The method according to claim 1, wherein the sample is not treated by denaturation treatment with heat, pH conditions or denaturing agent prior to adding the protease.

18. The method according to claim 1, wherein the sample is not treated by an organic solvent prior to adding the protease, the sample is not treated by reduction treatment prior to adding the protease, and the sample is not treated by increase or decrease in salt concentration prior to adding the protease.

19. A method of detecting proteins in a serum or plasma sample via mass spectrometry, comprising:
   adding a protease to the sample, thereby obtaining a mixture of digested peptides and undigested proteins, wherein the sample is not treated by an organic solvent prior to adding the protease, the sample is not treated by reduction treatment prior to adding the protease, the sample is not treated by increase or decrease in salt concentration prior to adding the protease, and the method does not comprise a protein or peptide enrichment step prior to or after adding the protease;
   separating the digested peptides in the mixture from the undigested proteins; and
   subjecting the digested peptides to mass spectrometry.

* * * * *